United States Patent [19]

Nishimura et al.

[11] Patent Number: 5,571,527
[45] Date of Patent: Nov. 5, 1996

[54] GRANULAR AGENT FOR RUMINANTS AND PROCESS FOR PRODUCING THE SAME

[75] Inventors: Kunio Nishimura; Toshio Morita, both of Kawasaki, Japan

[73] Assignee: Showa Denko K. K., Tokyo, Japan

[21] Appl. No.: 223,178

[22] Filed: Apr. 5, 1994

Related U.S. Application Data

[63] Continuation-in-part of Ser. No. 219,699, Mar. 30, 1994, abandoned, which is a continuation of Ser. No. 856,728, Mar. 24, 1992, abandoned.

[30] Foreign Application Priority Data

Mar. 25, 1991  [JP]  Japan .................................. 3-84778

[51] Int. Cl.$^6$ .................................................. A23K 1/18
[52] U.S. Cl. .................. 424/438; 424/489; 424/490; 424/498; 426/807
[58] Field of Search .................. 424/438, 489, 424/490, 498; 426/807

[56] References Cited

U.S. PATENT DOCUMENTS

| | | | |
|---|---|---|---|
| 4,533,557 | 8/1985 | Maruyama et al. | 426/61 |
| 4,713,245 | 12/1987 | Ando | 424/438 |
| 4,842,863 | 6/1989 | Nishimura | 424/438 |
| 4,948,589 | 8/1990 | Iijima | 424/438 |
| 4,996,067 | 2/1991 | Kobayashi | 426/96 |

FOREIGN PATENT DOCUMENTS

| | | |
|---|---|---|
| 452224 | 12/1974 | Japan . |
| 561057 | 1/1981 | Japan . |
| 175449 | 10/1983 | Japan . |
| 198946 | 11/1984 | Japan . |
| 168350 | 8/1985 | Japan . |
| 37054 | 2/1986 | Japan . |
| 2153199 | 8/1985 | United Kingdom . |

*Primary Examiner*—D. Gabrielle Phelan
*Attorney, Agent, or Firm*—Sughrue, Mion, Zinn, Macpeak & Seas

[57] ABSTRACT

Disclosed is the feed or feed additive granular agent containing a physiologically active substance and a coating layer having a laminar structure in which the tabular crystals are arranged in a laminated state. The coating layer comprises (a) one or more substances selected from the group consisting of a specific fatty acid or ester thereof, a specific animal or vegetable fat and fatty oil which may be hardened by hydrogenation, and a specific wax, and (b) tabular crystals of a substance which is sparingly water-soluble under a neutral condition but is readily water-soluble under an acidic condition and which has an average particle size of 5 to 30 μm, wherein said coating layer is present in a coating ratio of 5% by weight or more and 50% by weight or less, wherein said first coating material and said second coating material are in a proportion of 3:2 to 1:3 by weight, and process for producing the same. The granular agent has a high mechanical strength, increased durability in the rumen and superiority in solubility and absorption of the phisiologically active substance of said agent in the abomasum or downstream thereof resulting in efficient breeding, growth, or lactation of ruminants.

24 Claims, 1 Drawing Sheet

GRANULAR AGENT FOR RUMINANTS AND PROCESS FOR PRODUCING THE SAME

This is a Continuation-in-Part of application Ser. No. 08/219,699, filed Mar. 30, 1994, now abandoned, which is a file wrapper continuation of application Ser. No. 07/856,728, filed Mar. 24, 1992, now abandoned.

BACKGROUND OF THE INVENTION

1. Field of the Invention

The present invention relates to a granular agent for ruminants and containing a physiologically active substance which agent is used as a feed or feed additive for ruminants, and process for producing the same. More particularly, the present invention relates to a so-called rumen-bypass granular agent, i.e., an agent in which the physiologically active substance is protected and which is not solubilized in the rumen and is dissolved and absorbed in the abomasum and downstream thereof, and process for producing the same.

2. Description of the Prior Arts

It is known that when physiologically active substances such as amino acids and proteins are orally fed to ruminants, the substances are decomposed by microorganisms and enzymes in the rumens to lose their physiological activities inherent thereto.

Therefore, various granular agents for use in feeds or feed additives for ruminants have been proposed which agents are coated with protective substances that protect them from rumen juice and are dissolved and absorbed in a digestive organ including an abomasum and downstream thereof.

For example, Japanese Patent Publication No. 45224/1974 discloses a production method of an amino acid-containing oil capsule in which an amino acid or polypeptide is dispersed in a molten mixture of a fat and fatty oil having a melting point of 40° C. or higher and another fat and fatty oil having a melting point of lower than 40° C., and the resulting dispersion is poured into water kept at a temperature of between 20° C. and 40° C.

Japanese Patent Publication No. 1057/1981 discloses a granular agent containing a biologically useful substance coated with a matrix comprised by a saturated linear or branched, substituted or unsubstituted aliphatic monocarboxylic acid having at least 14 carbon atoms or salts thereof, or a mixture of such with an unsaturated linear or branched, substituted or unsubstituted aliphatic monocarboxylic acid having at least 14 carbon atoms or salts thereof.

U.S. Pat. No. 4,533,557 (Japanese Patent Application Laid-Open No. 175449/1983) discloses a additive composition for ruminant feeds which comprises a physiologically active substance dispersed in a protective matrix containing chitosan and one or more substances selected from the group consisting of a linear or branched, saturated or unsaturated monocarboxylic acid having 14 to 22 carbon atoms, a hardened vegetable oil and a hardened animal oil in which the protective substance is contained in an amount of 50 to 500 parts by weight per 100 parts by weight of the physiologically active substance, and the amount of chitosan in the protective substance is 0.1 to 90% by weight based on total protective substance.

British Patent Application No. 8501483 (British Patent Application No. 2153199A, Japanese Patent Application Laid-Open No. 168350/1985) discloses granular materials containing a substance useful for a living organism and 20% by weight or more of a water-insoluble salt of a physiologically acceptable acid which has an acidity weaker than hydrochloric acid (such as tertiary calcium phosphate, secondary calcium phosphate, tertiary magnesium phosphate, zinc phosphate, aluminum phosphate, calcium silicate, calcium pyrophosphate, magnesium carbonate, lead carbonate, cobalt carbonate, etc.), and 10% by weight or more of at least one substance selected from the group consisting of a linear or branched, saturated or unsaturated monocarboxylic acid having 14 carbon atoms or more or salts thereof, an animal or vegetable fat and fatty oil having a melting point of 40° C. or higher, and wax having a melting point of 40° C. or higher.

Japanese Patent Application Laid-Open No. 198946/1984 discloses a feed additive containing granules of a physiologically active substance coated with a film which is difficult to dissolve in a neutral or alkaline water but is readily soluble in an acidic water, in which the film is (1) an organic film formed from a film-forming component composed of linear or branched, substituted or unsubstituted, saturated or unsaturated aliphatic monocarboxylic acids having 14 to 22 carbon atoms containing one or more substances selected from one or more of aminocelluloses, polyvinyl-α-aminoacetates and polyvinylamines, or one or more substances selected from the group of aminocelluloses, polyvinylaminoacetates, polyvinylamines and chitosan, and one or more substances selected from the group consisting of hardened vegetable fats and fatty oils, and hardened animal fats and fatty oils, and (2) a film made of one or more inorganic substances selected from metal hydroxides and alkaline metal salts, and a binder, which film is further impregnated or coated with one or more substances selected from the group consisting of aminocelluloses, aminoacetates, vinylamines, aliphatic monocarboxylic acids having 14 to 22 carbon atoms, hardened vegetable fats and fatty oils, hardened animal fats and fatty oils, waxes, beeswaxes, ester gums and water-insoluble binders.

Japanese Patent Application Laid-Open No. 37054/1986 discloses particles of a feed additive containing (A) a physiologically active substance, (B) a substance which is stable under a neutral condition but is disintegrated or dissolved under a weakly acidic condition, and (C) at least one substance selected from linear or branched, saturated or unsaturated monocarboxylic acids having 14 carbon atoms or more or salts thereof, animal and vegetable fats and fatty oils having a melting point of 40° C. or higher, and waxes having a melting point of 40° C. or higher, in which 20% or less of particle size from the surface of each granule is occupied by a coating film made of 10% by weight or more of (B) and 90% by weight or less of (C).

However, the aforementioned prior arts have problems that the granular agents each have insufficient strengths and insufficient solubilities.

That is, in Japanese Patent Publications Nos. 45224/1974 and 1057/1981, while the disintegration of the film substances was expected to take place in a small intestine or downstream thereof, digestion and absorption of the objective substance tended to occur insufficiently.

Also, in U.S. Pat. No. 4,533,557 (Japanese Patent Application Laid-Open No. 175449/1983) and British Patent Application No. 2153199A (Japanese Patent Application Laid-Open No. 168350/1985), use was made of a substance which is capable of being disintegrated to release a physiologically active substance in an abomasum in order to overcome the aforementioned disadvantages, but the disintegration of such substance is insufficient. On the other hand, increase in the solubility results in the loss of durability in the rumen, and therefore no granular composition has been obtained that has both sufficient durability and sufficient solubility. In addition, among the physiologically active substances, it is impossible to increase the content of those substances which have high solubilities under neutral conditions.

In Japanese Patent Applications Laid-Open Nos. 198946/1984 and 37054/1986, the granules are coated in order to increase the content of the physiologically active substances and improve the durability in the rumen, and in order to increase the solubility (releasability) in the abomasum and downstream thereof, use is made in the coating layer of a solubility controlling substance which is sparingly soluble in a neutral or alkaline water but is readily soluble in an acidic water. In the granular agents disclosed in the aforementioned publications, while the increase in the durability in a rumen depends on the insolubility in water of fats and fatty oils used in the coating, the presence of the solubility controlling substance in the coating layer results in insufficient coating, and provides insufficient means for reducing the occurrence of cracks or the like in the coating layer due to the crystallinity of the fats and fatty oils themselves. For this reason, the increase in the durability of the granular agent in a rumen requires the increase in the coating amount, which makes poor the solubility of the granular agent in an abomasum and downstream thereof.

Therefore, it is an object of the present invention to provide a rumen bypass granular agent which can give a physiologically active substance to ruminants efficiently, that is, a granular agent for ruminants which is not solubilized in the rumen but is dissolved, digested and absorbed in the abomasum and downstream thereof. It is also an object of the present invention to provide a process for producing said granular agent for ruminants.

DISCLOSURE OF INVENTION

SUMMARY OF THE INVENTION

As a result of extensive investigations, it has now been found that a granular agent comprised by a core granular agent containing a physiologically active substance coated with a coating layer comprising specified fats and fatty oils, and laminar, tabular crystals of a substance which is sparingly water-soluble under neutral conditions but is readily water-soluble under acidic conditions is free of the above-described disadvantages and suitable as feeds or additive for feeds for ruminants, thus completing the present invention.

That is, the present invention provides a granular agent for ruminants, comprising a core granular agent containing a physiologically active substance coated with a coating layer comprising (a) a first coating material composed of one or more substances selected from the group consisting of a fatty acid having 12 to 22 carbon atoms or ester thereof, an animal or vegetable fat and fatty oil or a hardened animal or vegetable fat and fatty oil, having a melting point of 40° C. or higher, and a wax having a melting point of 40° C. or higher, and (b) a second coating material composed of tabular crystals of a substance which is sparingly water-soluble under a neutral condition but is readily water-soluble under an acidic condition and which has an average particle size of 5 to 30 μm, wherein said coating layer has a laminar structure in which said tabular crystals are arranged in a laminated state, wherein said first coating material and said second coating material are in a proportion of 3:2 to 1:3 by weight, and wherein said coating layer is present in a coating ratio of 5% by weight or more and 50% by weight or less, based on the total weight of the granular agent.

The present invention also provides a process for producing a granular agent for ruminants comprising a core granular agent containing a physiologically active substance and a coating layer, which comprises providing a core granular agent containing said physiologically active substance, and coating said core granular agent in a form in which said core granular agent is covered by a coating layer comprising (a) a first coating material composed of one or more substances selected from the group consisting of a fatty acid having 12 to 22 carbon atoms or ester thereof, an animal or vegetable fat and fatty oil or a hardened animal or vegetable fat and fatty oil, having a melting point of 40° C. or higher, and a wax having a melting point of 40° C. or higher, and (b) a second coating material composed of tabular crystals of a substance which is sparingly water-soluble under a neutral condition but is readily water-soluble under an acidic condition and which has an average particle size of 5 to 30 μm, wherein said coating layer has a laminar structure in which said tabular crystals are arranged in a laminated state, wherein said first coating material and said second coating material are in a proportion of 3:2 to 1:3 by weight, and wherein said coating layer is present in a coating ratio of 5% by weight or more and 50% by weight or less, based on the total weight of the granular agent.

The present invention also provides a granular agent for ruminants comprising a core granular agent containing a physiologically active substance coated with a coating layer comprising (a) a first coating material composed of one or more substances selected from the group consisting of a fatty acid having 12 to 22 carbon atoms or ester thereof, an animal or vegetable fat and fatty oil or a hardened animal or vegetable fat and fatty oil, having a melting point of 40° C. or higher, and a wax having a melting point of 40° C. or higher, and (b) a second coating material composed of tabular crystals of a substance which is sparingly water-soluble under a neutral condition but is readily water-soluble under an acidic condition and which has an average particle size of 5 to 30 μm, wherein the dissolution rate of a physiologically active substance of said granular agent is not higher than 50 % when measured under the condition consisting of pH 7.1, 39 ° C. and 18 hours, and the dissolution rate of said substance of said granular agent is not lower than 20% when measured under the condition consisting of pH 2, 39° C. and 18 hours.

The present invention also provides a granular agent used for growing or increasing lactation of ruminants comrising a core granular agent containing a physiologically active substance coated with a coating layer comprising (a) a first coating material composed of one or more substances selected from the group consisting of a fatty acid having 12 to 22 carbon atoms or ester thereof, an animal or vegetable fat and fatty oil or a hardened animal or vegetable fat and fatty oil, having a melting point of 40° C. or higher, and a wax having a melting point of 40° C. or higher, and (b) a second coating material composed of tabular crystals of a substance which is sparingly water-soluble under a neutral condition but is readily water-soluble under an acidic condition and which has an average particle size of 5 to 30 μm, wherein the dissolution rate of a physiologically active substance of said granular agent is not higher than 50% when measured under the condition consisting of pH 7.1, 39° C. and 18 hours, and the dissolution rate of said substance of said granular agent is not lower than 20% when measured under the condition consisting of pH 2, 39° C. and 18 hours.

The present invention also provides granular agent used for growing or increasing lactation of ruminants comrising a core granular agent containing a physiologically active substance coated with a coating layer comprising (a) a first coating material composed of one or more substances selected from the group consisting of a fatty acid having 12 to 22 carbon atoms or ester thereof, an animal or vegetable fat and fatty oil or a hardened animal or vegetable fat and fatty oil, having a melting point of 40° C. or higher, and a wax having a melting point of 40° C. or higher, and (b) a second coating material composed of tabular crystals of a substance which is sparingly water-soluble under a neutral condition but is readily water-soluble under an acidic condition and which has an average particle size of 5 to 30 μm, wherein said physiologically active substance is at least one substance selected from the group consisting of amino acid, derivative of amino acid, vitamin, derivative of vitamin, enzyme, animal drug, hormone, carbohydrate, other nutrient source, microorganism and mineral.

DETAILED DESCRIPTION OF THE INVENTION

Figure 1:
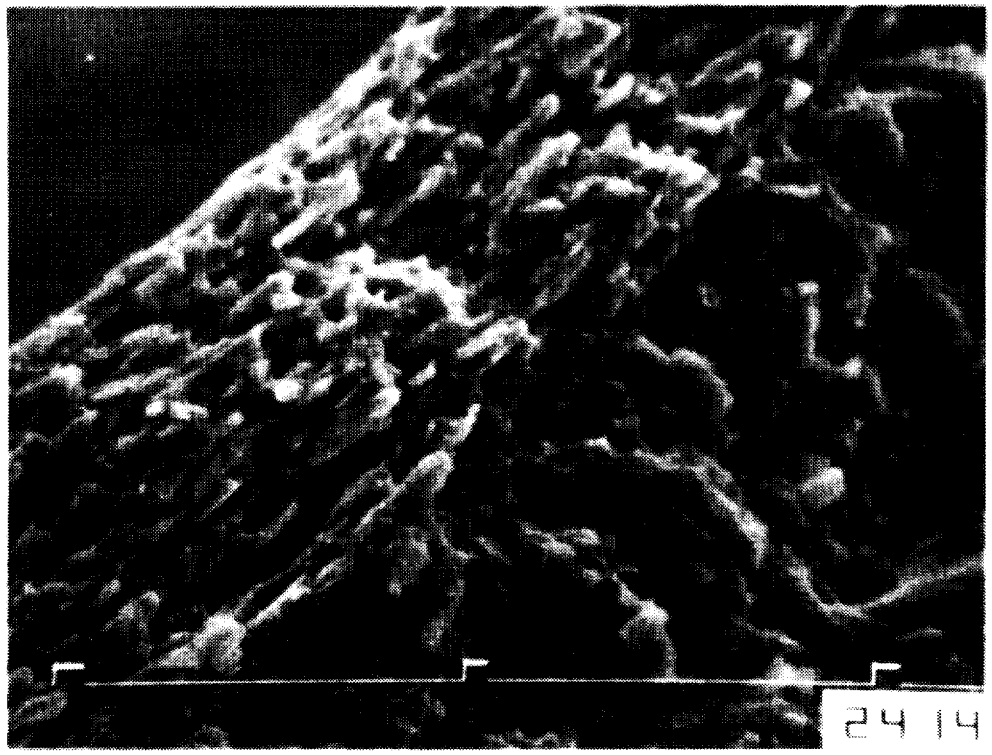
FIG. 1 is a cross-sectional photograph of the granular agent of Example 1 which consists of a coated granular agent containing lysine hydrochloride with tabular crystals of secondary calcium phosphate dihydrate of 10 μm as a coating substance by scanning electron micrography (magnification: ×500; the pitch indicated by a horizontal solid line in the bottom of the photo equals 100 μm), illustrating that the granular agent had a laminar structure in the coating layer in which the tabular crystals were arranged in a laminated state.

Hereafter, the present invention will be described in detail.

The physiologically active substance as used herein refers to any nutrient sources or feeds or drugs containing such nutrient sources so far as they are not in a liquid state.

Examples of the physiologically active substance include the following:

(1) Natural amino acid and derivative of amino acid: Alanine, glycine, glutamine, glutamic acid, arginine, methionine, lysine, tryptophan, valine, leucine, isoleucine, histidine, threonine, phenylalanine and other amino acids usable as feed additives, N-acylamino acids, hydroxy homologue compounds, hydrochloride salts, ammonium salts, and sodium salts of amino acids, and so on.

(2) Vitamin and the derivative of vitamine: Vitamin A, vitamin A palmitate, vitamin A acetate, β-carotene, vitamin Ds ($D_2$, $D_3$, $D_4$), vitamin E, menadione sodium bisulfite, vitamin Bs (thiamin, thiamin hydrochloride, riboflavin, nicotinic acid, nicotinic amide, calcium pantothenate, choline pantothenate, choline chloride or other choline salts, pyridoxine hydrochloride, cyanocobalamin, biotin, folic acid, p-aminobenzoic acid), vitamin K, vitamin Q, vitamin F, vitamin C, etc.

(3) Enzyme: Protease, amylase, lipase, cellulase, other physiologically effective enzymes, etc.

(4) Animal drug: Tetracycline type, amino sugar type, and macrolide type antibiotics; other drugs such as polypeptide type and polysaccharide type drugs; antiparasitics such a negphon; piperazine salts; etc.

(5) Hormone: Estrogen, stibestrol, hexestrol, tyroprotein, goitradien, etc.

(6) Nutrient source: Proteins, carbohydrates, etc.

(7) Useful microorganism: Lactobacillus, *Lactobacillus bifidus*, yeasts such as brewers' yeast, and so on.

(8) various mineral:

These physiologically active substances may be used alone or as mixtures of two or more of them.

The content of each physiologically active substance differs in its solubility. Therefore its optimum content can be determined at every physiologically active substance.

The core granular agent containing the physiologically active substance used in the present invention refers to a granular agent prepared from the aforementioned physiologically active substance, one or more optional excipients and a binder and the like.

The core granular agent can be prepared by using any conventional methods known in the art, for example, tumbling granulation, extruding granulation, compression granulation, fluidizing granulation, grinding granulation, agitation granulation, etc.

Upon granulation, a wide variety of excipients and binders usually used in this field of the art can be used. The tabular crystals, which are essential components of the granular agent of the present invention, may be ones which also function as the excipient and the fats and fatty oils may be ones which also function as the binder.

In the present invention, the core granular agent can be coated by using a fumbling granulator or an agitation granulator, more particularly by repeatedly adding the fats and fatty oils usually in a molten state and tabular crystals alternately to the core granular agent containing the physiologically active substance at a temperature by about 5° to 10° C. lower than the melting points of the fats and fatty oils, followed by cooling and solidification to form coating layers repeatedly.

Specific examples of the fats and fatty oils used in the present invention, i.e., one or more of the fatty acid having 12 to 22 carbon atoms or ester thereof, animal or vegetable fat and fatty oil or hardened animal or vegetable fat and fatty oil having a melting point of 40° C. or higher, and wax having a melting point of 40° C. or higher include, as the fatty acid having 12 to 22 carbon atoms or ester thereof, lauric acid, myristic acid, palmitic acid, stearic acid, behenic acid, oleic acid, rinolic acid, rinoleic acid and esters thereof (glycerol mono-, di- and tri-fatty acid esters, propylene glycol fatty acid esters, sorbitan fatty acid esters, etc.); as the animal and vegetable fats and fatty oils having a melting point of 40° C. or higher: palm oil, beef tallow, porcine tallow, etc.; as the hardened animal and vegetable fats and fatty oils: hardened castor oil, hardened colza oil, hardened beef tallow, extremely hardened beef tallow, etc.; and as the wax: bee wax, carnauba wax, Japan wax, etc.

Among the fats and fatty oils, preferred are hardened animal and vegetable fats and fatty oils, with the extremely hardened beef tallow being particularly preferred.

In the present invention, the tabular crystals in the coating layers, i.e., tabular crystals of a substance which is sparingly water-soluble under a neutral condition but is readily water-soluble under an acidic condition and which has an average particle size of 5 to 30 μm, can be prepared by grinding or sifting tabular crystals of the substance which does not dissolve under a neutral condition but dissolves under an acidic condition. The average particle size as used herein refers to average particle size on weight basis measured using a usually used sedimentation particle size distribution analyzer after conversion into spheres.

Specific examples of the tabular crystals of the substance which is sparingly water-soluble under a neutral condition but is readily water-soluble under an acidic condition include tabular crystals of amino acid such as isoleucine, L-cystine, and methionine, and tabular crystals of inorganic salts such as secondary calcium phosphate dihydrate. Among these, tabular crystals of L-cystine and secondary calcium phosphate dihydrate are preferred.

As the excipient used upon granulation other than the tabular crystals which are essential components of the granular agent of the present invention, there can be cited, for example, at least one substance selected from the group consisting of carbonates such as calcium carbonate, magnesium carbonate, cobalt carbonate, and aluminum carbonate; inorganic salts such as tertiary calcium phosphate, secondary calcium phosphate, tertiary magnesium phosphate, secondary magnesium phosphate, zinc phosphate, aluminum phosphate, calcium silicate, and calcium pyrophosphate; metal oxides such as magnesium oxide, calcium oxide, and silicon dioxide; polysaccharides such as chitosan, chitin, calcium alginate and carrageenan; and synthetic high molecular weight substances such as cellulose derivatives, and polyvinyl derivatives.

The tabular crystals used in the present invention refers to crystals of which proportions of edges are in the range of 1:2:2 to 1:50:50 (H:L:D). Such tabular crystals can be obtained by adjusting the crystallization method. Also, the tabular crystals can be distinguished one from another by X-ray powder diffractometry. For example, in the case of secondary calcium phosphate dihydrate, the tabular crystals refer to those which have a diffraction strength ratio $I_{2.94}/I_{3.06}$ defined as a ratio between interplanar distances of 2.94 (Å) and 3.06 (Å) as measured by X-ray diffractometry (CuKα) is 0.3 or less.

In the case where use is made of a substance other than the tabular crystals of the substance which is sparingly water-soluble under a neutral condition but is readily water-soluble under an acidic condition upon the granulation, there is obtained no laminar structure in the coating layer in which such a substance is present in a laminated state, resulting in that the coated layer becomes brittle, and no sufficient durability in a rumen can be obtained unless the coated amount is increase. However, the increase in the coated amount in order to obtain increased durability results in insufficient solubility (releasability) of the physiologically active substance in the abomasum or downstream thereof.

Even when the tabular crystals of the substance of which solubility is as described above are used, those which have average particle sizes of 30 μm or larger suffer from insufficient coating of the tabular crystals with the oils and fats so that no laminar structure can be formed in the coating layers in which such a substance is present in a laminated state, thus giving a poor durability in the rumen. If the tabular crystals used have an average particle size of 5 μm or smaller, the solubility (releasability) of the physiologically active substance in the abomasum or downstream thereof is poor although a laminar structure is formed in the coating layers.

Proportion of the fats and fatty oils to the tabular crystals in the coating layers is preferably in the range of 3:2 to 1:3 by weight. If the tabular crystals are used in proportions more or less than the above proportion, thus failing to give sufficient effects because of a poor durability in the rumen or a poor solubility of the physiologically active substance in the abomasum and downstream thereof.

While the coating ratio of the core granular agent containing physiologically active substance should be determined depending upon the solubility of the physiologically active substance in the abomasum or downstream thereof, or characteristics of the core granular agent, and performance to be obtained, usually the coating ratio is 5% by weight or more and 50% by weight or less, based on the total weight of the granular agent, wherein the coating ratio is defined as the amount by weight of the coating layer to the amount by weight of the granular agent according to the present invention. If the coating ratio is less than 5% by weight, the durability in the rumen is poor and no sufficient effects can be obtained. On the other hand, if use is made of a large amount of the coating material as much as 50% by weight or more, the content of the effective ingredient decreases, which is not preferable from an economical viewpoint.

In the granular agent for feeds for ruminants and additives thereto according to the present invention, obtained by coating the core granular agent composed mainly of physiologically active substance with a coating layer comprising specified fats and fatty oils and tabular crystals of the substance which is sparingly water-soluble under a neutral condition and readily water-soluble under an acidic condition and having an average particle size of 5 to 30 μm, the fats and fatty oils in the coating layers function as a protective substance which increases the durability in the rumen. The aforementioned tabular crystals form a laminar structure in which they are present in a laminated state in the coating layers. The laminar structure strengthens the coating layers to increase not only the durability of the granular agent in the rumen but also the solubility (releasability) of the physiologically active substance in the abomasum or downstream thereof.

The dissolution rate of a physiologically active substance of said granular agent in the present invention is not higher than 50% when measured under the condition consisting of pH 7.1, 39° C. and 18 hours equivalent to rumen juice, and the dissolution rate of said substance of said granular agent is not lower than 20% when measured under the condition consisting of pH 2, 39° C. and 18 hours equivalent to abomasum juice. Preferably, the dissolution rate of a physiologically active substance of said granular agent in the present invention is not higher than 35% when measured under the condition consisting of pH 7.1, 39° C. and 18 hours, and the dissolution rate of said substance of said granular agent is not lower than 20% when measured under the condition consisting of pH 2, 39° C. and 18 hours. More preferably, the dissolution rate of a physiologically active substance of said granular agent in the present invention is not higher than 35% when measured under the condition consisting of pH 7.1, 39° C. and 18 hours, and the dissolution rate of said substance of said granular agent is not lower than 30% when measured under the condition consisting of pH 2, 39° C. and 18 hours. Most preferably, the dissolution rate of a physiologically active substance of said granular agent in the present invention is not higher than 30% when measured under the condition consisting of pH 7.1, 39° C. and 18 hours, and the dissolution rate of said substance of said granular agent is not lower than 40% when measured under the condition consisting of pH 2, 39° C. and 18 hours.

The granular agent for ruminants according to the present invention exhibits excellent performance as a rumen-bypass granular agent for ruminants, and can be dissolved to release a physiologically active substance useful as a feed or additive thereto in an abomasum or downstream thereof, thus allowing the physiologically active substance to be digested and absorbed efficiently.

BEST MODE FOR CARRYING OUT THE INVENTION

The present invention will be described in greater detail by examples and comparative examples. However, the present invention should not be construed as being limited thereto.

(1) Granulation of a core granular agent containing a physiologically active substance:

(a) Granulation of a core granular agent containing lysine hydrochloride:

1,500 g of L-lysine hydrochloride and 540 g of extremely hardened beef tallow were granulated using a tumbling granulator with heating to obtain a granular agent of 8 to 24 mesh.

(b) Granulation of a core granular agent containing anhydrous glucose:

1,200 g of anhydrous glucose, 75 g of calcium carbonate, 38 g of silicon dioxide and 300 g of extremely hardened beef tallow were granulated using a Henschel mixer with heating to obtain a granular agent of 8 to 24 mesh.

(c) Granulation of a core granular agent containing magnesium L-ascorbate phosphate (magnesium salt of L-ascorbyl- 2-phosphate):

L-ascorbic acid-2-phosphate Mg (product of Showa Denko K.K.) was used as an example of magnesium L-ascorbate phosphate.

1,000 g of magnesium L-ascorbate phosphate and 200 g of extremely hardened beef tallow were granulated using an agitation granulator with heating to obtain a granular agent of 8 to 24 mesh.

(d) Granulation of a core granular agent containing choline chloride:

1,000 g of choline chloride, 100 g of calcium carbonate, 100 g of silicon dioxide and 510 g of extremely hardened beef tallow were granulated using an agitation granulator with heating to obtain a granular agent of 8 to 24 mesh.

(e) Granulation of a core granular agent containing DL-methionine:

1,500 g of DL-methionine and 340 g of extremely hardened beef tallow were granulated using a spartan extruder with heating to obtain a granular agent of 8 to 24 mesh.

(f) Granulation of a core granular agent containing L-tryptophan:

1,500 g of L-tryptophan and 490 g of extremely hardened beef tallow were granulated by using an agitation granulator with heating to obtain a granular of 8 to 24 mesh.

(g) Granulation of a core granular agent containing nicotinic acid:

920 g of nicotinic acid, 32 g of calcium carbonate, 64 g of silicon dioxide and 312 g of extremely hardened beef tallow were granulated by using an agitation granulator with heating to obtain a granular agent of 8 to 24 mesh.

(h) Granulation of a core granular agent containing betaine:

1360 g of betaine, 250 g of calcium carbonate and 360 g of extremely hardened beef tallow were granulated by using an agitation granulator with heating to obtain a granular agent of 8 to 24 mesh.

(i) Granulation of a core granular agent containing vitamin C:

1500 g of vitamin C, 70 g of silicon dioxide and 320 g of extremely hardened beef tallow were granulated by using an agitation granulator with heating to obtain a granular agent of 8 to 24 mesh.

(j) Granulation of a core granular agent containing glycine and alanine:

650 g of glycine, 650 g of DL-alanine and 303 g of extremely hardened beef tallow were granulated by using an agitation granulator with heating to obtain a granular agent of 8 to 24 mesh.

(2) Coating of a core granulator containing a physiologically active substance:

EXAMPLES 1 to 3 and Comparative Examples 1 to 6

Granular Agent Consisting of a Coated Core Granular Agent Containing Lysine Hydrochloride In an agitation granulator were charged 1,500 g of a core granular agent containing lysine hydrochloride and the temperature of the material was kept at 50° C. by using main spindle alone of the granulator. Then, using molten extremely hardened beef tallow and nine (9) kinds of coating substances shown in Table 1 (Examples 1 to 3 and Comparative Examples 1 to 6), aliquots of the core granular agent were coated, respectively, to a coating ratio of 33% by weight based on the total weight of the resulting granules. The extremely hardened beef tallow and each of the coating substances shown in Table 1 were used in a proportion of 2:3 (by weight), and added alternately.

TABLE 1

| Coating Substance | |
|---|---|
| Example 1 | Tabular crystals of secondary calcium phosphate dihydrate (average particle diameter: 10 μm) |
| Example 2 | Tabular crystals of L-cystine (average particle size: 10 μm) |
| Example 3 | Tabular crystals of DL-methionine (average particle size: 10 μm) |
| Comparative Example 1 | Prismatic crystals of secondary calcium phosphate dihydrate (average particle diameter: 10 μm) |
| Comparative Example 2 | Tertiary calcium phosphate (amorphous) |
| Comparative Example 3 | Calcium carbonate (amorphous) |
| Comparative Example 4 | Tabular crystals of secondary calcium phosphate dihydrate (average particle diameter: 35 μm) |
| Comparative Example 5 | Tabular crystals of secondary calcium phosphate dihydrate (average particle diameter: 2 μm) |
| Comparative Example 6 | Non-tabular crystals of DL-Cystine (average particle size: 2 μm) |

Figure 2:
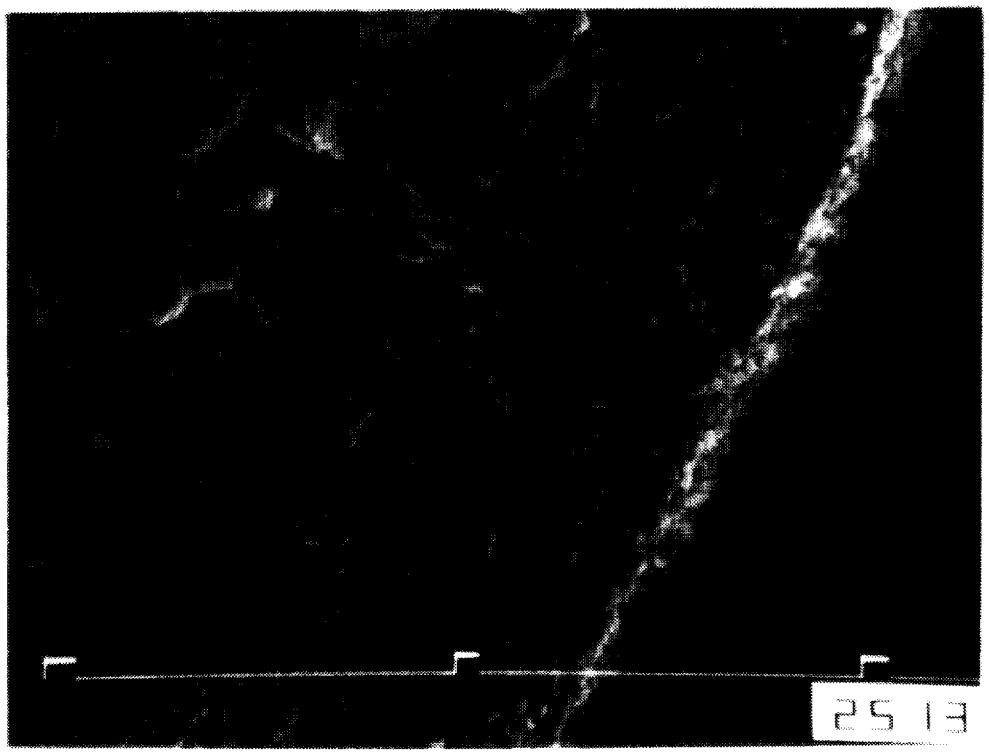
FIG. 2 is a cross-sectional photograph of the granular agent of Comparative Example 1 which consists of a coated granular agent containing lysine hydrochloride with prismatic crystals of secondary calcium phosphate dihydrate of 10 μm as a coating substance by scanning electron micrography (magnification: ×500; the pitch indicated by a horizontal solid line in the bottom of the photo equals 100 μm), illustrating that the granular agent did not have a laminar structure in the coating layer in which the tabular crystals were arranged in a laminated state.

Observation of the cross sections of the granular agents of Example 1 (FIG. 1) and Comparative Example 1 (FIG. 2) by scanning electron micrography (magnification: ×500) revealed that the granular agent of Example 1 using tabular crystals of secondary calcium phosphate dihydrate having an average particle size of 10 μm had a laminar structure in the coating layer in which the tabular crystals were arranged in a laminated state while in the granular agent of Comparative Example 1 using prismatic crystals no such laminar structure was found.

Also, scanning electron micrographic observation of the cross sections of the granular agents obtained in Examples 2 and 3 indicated that the respective coating layers of these granular agents showed laminar structures similar to the laminar structure found in the coating layer of the granular agent of Example 1.

Dissolution tests of the resulting granular agents were conducted in a mimic-rumen solution (in vitro), in a rumen of sheep (in vivo), in a mimic-abomasum solution (in vitro), respectively.

Test solutions and test method used are as follows.
(a) Dissolution Test Method

One gram (1 g) each of the granular agents containing physiologically active substances prepared previously was immersed in 50 ml each of the mimic-rumen solution and the mimic-abomasum solution, respectively, and the resulting mixtures were shaken at 39° C. for 18 hours. Thereafter, the physiologically active substances in the test solutions were quantitatively determined by high performance liquid chromatography, and dissolution rates thereof were obtained.
(b) Composition of the Mimic-Rumen Solution 6.3 g or primary sodium phosphate dihydrate, 30.5 g of secondary sodium phosphate, 6.2 g of primary potassium phosphate, 0.6 g of potassium chloride, 7.9 g of sodium chloride, 0.3 g of calcium chloride, 0.3 g of magnesium chloride, and 31.5 g of sodium bicarbonate were dissolved in water to make 3 liters. The pH of the resulting solution was 7.1.
(c) Composition of the Mimic-Abomasum Solution 20.5 g of sodium acetate, 8.8 g of sodium chloride, and 3 ml of 0.1 vol. % ethanol were dissolved in water to make 3 liters with adjusting pH to 2.
(d) Test Method for Solubility in the Rumen of Sheep One gram (1 g) of the granular agent previously prepared was put in a 200-mesh nylon bag, which was immersed for 24 hours in the rumen of rumen-fistulated-sheep. The physiologically active substance which remained in the granular agent was quantitatively determined by high performance liquid chromatography to obtain remaining rates which were converted to dissolution rates (%).

Results of the dissolution tests are shown in Table 2.

EXAMPLE 4

Granular Agent Consisting of a Coated Core
Granular Agent Containing Anhydrous Glucose In a tumbling granulator were charged 1,500 g of a core granular agent containing anhydrous glucose, and the temperature of the material was kept at 50° C. Coating of the core granular agent was performed using molten extremely hardened beef tallow and tabular crystals of secondary calcium phosphate dihydrate having a particle size of 10 μm in a proportion of 2:3 by weight in the same manner as in Example 1 to a coating ratio of 23% by weight. Dissolution tests of the resulting granular agent were conducted in the same manner as in Example 1. Results obtained are shown in Table 2.

EXAMPLE 5

Granular Agent Consisting of a Coated Core
Granular Agent Containing Magnesium L-ascorbate Phosphate Coating of a core granular agent containing magnesium L-ascorbate phosphate (magnesium salt of L-ascorbyl-2-phosphate) was performed in the same manner as in Example 1 using extremely hardened beef tallow and tabular crystals of secondary calcium phosphate dihydrate having a particle size of 10 μm in a proportion of 2:3 by weight to a coating ratio of 23% by weight. Dissolution tests of the resulting granular agent were conducted in the same manner as in Example 1. Results obtained are shown in Table 2.

EXAMPLE 6

Granular Agent Consisting of a Coated Core
Granular Agent Containing Choline Chloride Coating of a core granular agent containing choline chloride was performed in the same manner as in Example 1 using extremely hardened beef tallow and tabular crystals of secondary calcium phosphate dihydrate having a particle size of 10 μm in a proportion of 2:3 by weight to a coating ratio of 23% by weight. Dissolution tests of the resulting granular agent were conducted in the same manner as in Example 1. Results obtained are shown in Table 2.

EXAMPLE 7

Granular Agent Consisting of a Coated Core
Granular Agent Containing DL-methionine Coating of a core granular agent containing DL-methionine was performed in the same manner as in Example 1 using extremely hardened beef tallow and tabular crystals of secondary calcium phosphate dihydrate having a particle size of 10 μm in a proportion of 2:3 by weight to a coating ratio of 20% by weight. Dissolution tests of the resulting granular agent were conducted in the same manner as in Example 1. Results obtained are shown in Table 2.

EXAMPLE 8

Granular Agent Consisting of a Coated Core
Granular Agent Containing L-tryptophan Coating of a core granular agent containing L-tryptophan was performed in the same manner as in Example 1 using extremely hardened beef tallow and tabular crystals of secondary calcium phosphate dihydrate having a particle size of 10 μm in a proportion of 2:3 by weight to a coating ratio of 9% by weight. Dissolution tests of the resulting granular agent were conducted in the same manner as in Example 1. Results obtained are shown in Table 2.

EXAMPLE 9

Granular Agent Consisting of a Coated Core
Granular Agent Containing Nicotinic Acid Coating of a core granular agent containing nicotinic acid was performed in the same manner as in Example 1 using extremely hardened beef tallow and tabular crystals of secondary calcium phosphate dihydrate having a particle size of 10 μm in a proportion of 2:3 by weight to a coating ratio of 26% by weight. Dissolution tests of the resulting granular agent were conducted in the same manner as in Example 1. Results obtained are shown in Table 2.

EXAMPLE 10

Granular Agent Consisting of a Coated Core
Granular Agent Containing Betaine

Coating of a core granular agent containing betaine was performed in the same manner as in Example 1 using extremely hardened beef tallow and tabular crystals of secondary calcium phosphate dihydrate having a particle size of 10 μm in a proportion of 2:3 by weight to a coating ratio of 29% by weight. Dissolution tests of the resulting granular agent were conducted in the same manner as in Example 1. Results obtained are shown in Table 2.

EXAMPLE 11

Granular Agent Consisting of a Coated Core Granular Agent Containing Vitamin C Coating of a core granular agent containing vitamin C was performed in the same manner as in Example 1 using extremely hardened beef tallow and tabular crystals of secondary calcium phosphate dihydrate having a particle size of 10 μm in a proportion of 2:3 by weight to a coating ratio of 26% by weight. Dissolution tests of the resulting granular agent were conducted in the same manner as in Example 1. Results obtained are shown in Table 2.

EXAMPLE 12

Granular Agent Consisting of a Coated Core Granular Agent Containing Glycine and Alanine Coating of a core granular agent containing glycine and DL-alanine was performed in the same manner as in Example 1 using extremely hardened beef tallow and tabular crystals of secondary calcium phosphate dihydrate having a particle size of 10 μm in a proportion of 3:4 by weight to a coating ratio of 22% by weight. Dissolution tests of the resulting granular agent were conducted in the same manner as in Example 1. Results obtained are shown in Table 2.

EXAMPLE 13

Granular Agent Consisting of a Coated Core Granular Agent Containing Lysine Hydrochloride Coating of a core granular agent containing lysine hydrochloride was performed in the same manner as in Example 1 using extremely hardened beef tallow and tabular crystals of secondary calcium phosphate dihydrate having a particle size of 10 μm in a proportion of 2:3 by weight to a coating ratio of 26% by weight. Dissolution tests of the resulting granular agent were conducted in the same manner as in Example 1. Results obtained are shown in Table 2.

EXAMPLE 14

Granular Agent Consisting of a Coated Core Granular Agent Containing Lysine Hydrochloride Coating of a core granular agent containing lysine hydrochloride was performed in the same manner as in Example 1 using extremely hardened beef tallow and tabular crystals of secondary calcium phosphate dihydrate having a particle size of 10 μm in a proportion of 2:3 by weight to a coating ratio of 38% by weight. Dissolution tests of the resulting granular agent were conducted in the same manner as in Example 1. Results obtained are shown in Table 2.

TABLE 2

| Run | Physiologically Active Substance | Coating Material | Laminar Structure | Content of Physiologically Active Substance (wt. %) | Dissolution Rate (%) Mimic-Rumen Solution | Sheep Rumen | Mimic-Abomasum Solution |
|---|---|---|---|---|---|---|---|
| Example 1 | LysHCl*[1] | $CaHPO_4 \cdot 2H_2O$*[3] | Yes | 49 | 17 | 20 | 42 |
| Example 2 | LysHCl*[1] | L-Cystine*[3] | Yes | 49 | 24 | 25 | 43 |
| Example 3 | LysHCl*[1] | D,L-Met*[2]/*[3] | Yes | 49 | 25 | 27 | 44 |
| Example 4 | Glucose | $CaHPO_4 \cdot 2H_2O$*[3] | Yes | 57 | 17 | 11 | 55 |
| Example 5 | Magnesium L-ascorbate phosphate | $CaHPO_4 \cdot 2H_2O$*[3] | Yes | 64 | 18 | 20 | 58 |
| Example 6 | Choline chloride | $CaHPO_4 \cdot 2H_2O$*[3] | Yes | 45 | 17 | 20 | 49 |
| Example 7 | D,L-Met*[2] | $CaHPO_4 \cdot 2H_2O$*[3] | Yes | 65 | 12 | 18 | 47 |
| Example 8 | L-Tryptophan | $CaHPO_4 \cdot 2H_2O$*[3] | Yes | 68 | 12 | 28 | 48 |
| Example 9 | Nicotinic acid | $CaHPO_4 \cdot 2H_2O$*[3] | Yes | 51 | 10 | 16 | 50 |
| Example 10 | Betaine | $CaHPO_4 \cdot 2H_2O$*[3] | Yes | 48 | 14 | 18 | 44 |
| Example 11 | Vitamin C | $CaHPO_4 \cdot 2H_2O$*[3] | Yes | 58 | 19 | 25 | 51 |
| Example 12 | Glycine/DL-Alanine | $CaHPO_4 \cdot 2H_2O$*[3] | Yes | 62 | 20 | 27 | 40 |
| Example 13 | LysHCl*[1] | $CaHPO_4 \cdot 2H_2O$*[3] | Yes | 54 | 42 | 45 | 58 |
| Example 14 | LysHCl*[1] | $CaHPO_4 \cdot 2H_2O$*[3] | Yes | 46 | 24 | 25 | 28 |
| Comparative Example 1 | LysHCl*[1] | $CaHPO_4 \cdot 2H_2O$ (prismatic) | No | 49 | 94 | 98 | 86 |
| Comparative Example 2 | LysHCl*[1] | $Ca_3(PO_4)_2$ (amorphous) | No | 49 | 71 | 75 | 80 |
| Comparative Example 3 | LysHCl*[1] | $CaCO_3$ (amorphous) | No | 49 | 75 | 77 | 82 |
| Comparative Example 4 | LysHCl*[1] | $CaHPO_4 \cdot 2H_2O$*[3] (35 μm) | No | 49 | 55 | 41 | 60 |
| Comparative Example 5 | LysHCl*[1] | $CaHPO_4 \cdot 2H_2O$*[3] (2 μm) | Yes | 49 | 20 | 26 | 19 |
| Comparative Example 6 | LysHCl*[1] | DL-Cystine (2 μm) | No | 49 | 93 | 98 | 90 |

Notes:
*[1]: L-lysine hydrochloride;
*[2]: DL-methionine;
*[3]: tabular crystals

INDUSTRIAL APPLICABILITY

The present inventions provides a feed or feed additive granular agent for ruminants having a strengthened coating layer and an excellent rumen bypass property, which agent comprises a core granular agent containing a physiologically active substance coated with a coating layer comprising (a) one or more substances (a first coating material) selected from the group consisting of a fatty acid having 12 to 22 carbon atoms or ester thereof, an animal or vegetable fat and fatty oil or a hardened animal or vegetable fat and fatty oil, having a melting point of 40° C. or higher, and a wax having a melting point of 40° C. or higher, and (b) tabular crystals of a substance (a second coating material) which is sparingly water-soluble under a neutral condition but is readily water-soluble under an acidic condition and which has an average particle size of 5 to 30 μm, the first coating material and the second coating material being in a proportion of 3:2 to 1:3 by weight, wherein said coating layer is present in a coating ratio of 5% by weight or more ad 50% by weight or less, and the coating layer having a laminar structure in which the tabular crystals are arranged in a laminated state, and process for producing the same.

The granular agent for ruminants according to the present invention enables ruminants to directly or effectively absorb physiologically active substances useful to the ruminants and the use of the granular agent makes it possible to breed or grow ruminants efficiently or increase lactation of ruminants efficiently, which is very important industrially.

What is claimed is:

1. A granular agent for ruminants, comprising a core granular agent containing a physiologically active substance coated with a coating layer comprising:

(a) a first coating material composed of one or more substances selected from the group consisting of a fatty acid having 12 to 22 carbon atoms or ester thereof, an animal or vegetable fat and fatty oil or a hardened animal or vegetable fat and fatty oil, having a melting point of 40° C. or higher, and a wax having a melting point of 40° C. or higher, and (b) a second coating material composed of tabular crystals of a substance which is sparingly water-soluble under a neutral condition but is readily water-soluble under an acidic condition and which has an average particle size of 5 to 30 μm, wherein said coating layer has a laminar structure in which said tabular crystals are arranged in a laminated state, wherein said first coating material and said second coating material are in a proportion of 3:2 to 1:3 by weight, wherein said coating layer is present in a coating ratio of 5% by weight or more and 50% by weight or less, based on the total weight of the granular agent, and wherein said physiologically active substance of said granular agent has a dissolution rate not higher than 50% when measured under conditions consisting of pH 7.1, 39° C. and 18 hours, and a dissolution rate not lower than 20% when measured under conditions consisting of pH 2, 39° C. and 18 hours.

2. The granular agent for ruminants as claimed in claim 1, wherein said physiologically active substance is at least one substance selected from the group consisting of an amino acid, a derivative of an amino acid selected from the group consisting of an N-acylamino acid, a hydroxy homologue compound, a hydrochloride salt of an amino acid, an ammonium salt of an amino acid and a sodium salt of an amino acid, a vitamin, a derivative of a vitamin selected from the group consisting of vitamin A palmitate, vitamin A acetate, menadione sodium bisulfite, thiamine hydrochloride, pyridoxine hydrochloride and p-aminobenzoic acid, an enzyme, an animal drug, a hormone, a carbohydrate, a nutrient protein, a microorganism and a mineral.

3. A granular agent for ruminants as claimed in claim 1 or 2, wherein said second coating material is at least one substance selected from the group consisting of isoleucine, cystine, methionine, and secondary calcium phosphate dihydrate.

4. A granular agent for ruminants as claimed in claim 1, wherein said animal or vegetable fat and fatty oil is at least one substance selected from the group consisting of palm oil, beef tallow and porcine tallow.

5. A granular agent for ruminants as claimed in claim 1, wherein said hardened animal or vegetable fat and fatty oil is at least one substance selected from the group consisting of hardened castor oil, hardened colza oil, hardened beef tallow, and extremely hardened beef tallow.

6. A granular agent for ruminants as claimed in claim 1, wherein said wax having a melting point of 40° C. or higher is at least one substance selected from the group consisting of bee wax, carnauba wax, and Japan wax.

7. A granular agent for ruminants as claimed in claim 1, produced by a process which comprises providing a core granular agent containing said physiologically active substance, and coating said core granular agent with a coating layer comprising said first coating material and said second coating material in such a way as that said coating layer has laminar structure and that said tabular crystals are arranged in a laminated state in said coating layer.

8. A process for producing a granular agent for ruminants comprising a core granular agent containing a physiologically active substance and a coating layer, which comprises providing a core granular agent containing said physiologically active substance, and coating said core granular agent in a form in which said core granular agent is covered by a coating layer comprising:

(a) a first coating material composed of one or more substances selected from the group consisting of a fatty acid having 12 to 22 carbon atoms or ester thereof, an animal or vegetable fat and fatty oil or a hardened animal or vegetable fat and fatty oil, having a melting point of 40° C. or higher, and a wax having a melting point of 40° C. or higher, and (b) a second coating material composed of tabular crystals of a substance which is sparingly water-soluble under a neutral condition but is readily water-soluble under an acidic condition and which has an average particle size of 5 to 30 μm, wherein said coating layer has a laminar structure in which said tabular crystals are arranged in a laminated state, wherein said first coating material and said second coating material are in a proportion of 3:2 to 1:3 by weight, wherein said coating layer is present in a coating ratio of 5% by weight or more and 50% by weight or less, based on the total weight of the granular agent, and wherein said physiologically active substance of said granular agent has a dissolution rate not higher than 50% when measured under conditions consisting of pH 7.1, 39° C. and 18 hours, and a dissolution rate not lower than 20% when measured under conditions consisting of pH 2, 39° C. and 18 hours.

9. The process for producing a granular agent for ruminants as claimed in claim 8, wherein said physiologically active substance is at least one substance selected from the group consisting of an amino acid, a derivative of an amino acid selected from the group consisting of an N-acylamino acid, a hydroxy homologue compound, a hydrochloride salt of an amino acid, an ammonium salt of an amino acid and a sodium salt of an amino acid, a vitamin, a derivative of a vitamin selected from the group consisting of vitamin A palmitate, vitamin A acetate, menadione sodium bisulfite, thiamine hydrochloride, pyridoxine hydrochloride and p-aminobenzoic acid, an enzyme, an animal drug, a hormone, a carbohydrate, a nutrient protein, a microorganism and a mineral.

10. A process for producing a granular agent for ruminants as claimed in claim 9, wherein said amino acid is at least one substance selected from the group consisting of alanine, glycine, lysine, methionine, tryptophan, arginine, threonine, valine, leucine, isoleucine, histidine, phenylalanine, glutamine, and glutamic acid, wherein said vitamine is at least one substance selected from the group consisting of vitamin A, β-carotene, thiamin, riboflavin, pyridoxine, cyanocobalamin, vitamin D, vitamin E, vitamin K, choline, choline chloride or other choline salt, vitamin C, magnesium salt of L-ascorbyl-2-phosphate, betain, nicotinic acid, nicotinic amide, folic acid, biotin, and pantothenate.

11. A process for producing a granular agent for ruminants as claimed in claim 9, wherein said physiologically active substance is at least one substance selected from the group consisting of alanine, glycine, lysine or lysine hydrochloride, methionine, tryptophan, choline chloride, vitamin C, magnesium salt of L-ascorbyl- 2-phosphate, betaine, nicotinic acid, and glucose.

12. A process for producing a granular agent for ruminants as claimed in claim 8, wherein said substance which is sparingly water-soluble under a neutral condition but readily water-soluble under an acidic condition is at least one substance selected from the group consisting of isoleucine, L-cystine, methionine, and secondary calcium phosphate dihydrate.

13. A process for producing a granular agent for ruminants as claimed in claim 8, wherein said amimal or vegetable fat and fatty oil is at least one substance selected from the group consisting of palm oil, beef tallow and porcine tallow.

14. A process for producing a granular agent for ruminants as claimed in claim 8, wherein said hardened animal or vegetable fat and fatty oil is at least one substance selected from the group consisting of hardened castor oil, hardened colza oil, hardened beef tallow, and extremely hardened beef tallow.

15. A process for producing a granular agent for ruminants as claimed in claim 8, wherein said wax having a melting point of 40° C. or higher is at least one substance selected from the group consisting of bee wax, carnauba wax, and Japan wax.

16. A granular agent for ruminants as claimed in claim 2, wherein said amino acid is at least one substance selected from the group consisting of alanine, glycine, lysine, methionine, tryptophan, arginine, threonine, valine, leucine, isoleucine, histidine, phenylalanine, glutamine, and glutamic acid, wherein said vitamine is at least one substance selected from the group consisting of vitamin A, β-carotene, thiamin, riboflavin, pyridoxine, cyanocobalamin, vitamin D, vitamin E, vitamin K, choline, choline chloride or other choline salt, vitamin C, magnesium salt of L-ascorbyl-2-phosphate, betain, nicotinic acid, nicotinic amide, folic acid, biotin, and pantothenate.

17. A granular agent for ruminants as claimed in claim 1, wherein said physiologically active substance is at least one substance selected from the group consisting of alanine, glycine, lysine or lysine hydrochloride, methionine, tryptophan, choline chloride or other choline salt, vitamin C, magnesium salt of L-ascorbyl-2-phosphate, betaine, nicotinic acid, and glucose.

18. A granular agent used for growing or increasing lactation of ruminants comprising a core granular agent containing a physiologically active substance coated with a coating layer comprising:

(a) a first coating material composed of one or more substances selected from the group consisting of a fatty acid having 12 to 22 carbon atoms or ester thereof, an animal or vegetable fat and fatty oil or a hardened animal or vegetable fat and fatty oil, having a melting point of 40° C. or higher, and a wax having a melting point of 40° C. or higher, and (b) a second coating material composed of tabular crystals of a substance which is sparingly water-soluble under a neutral condition but is readily water-soluble under an acidic condition and which has an average particle size of 5 to 30 μm, wherein the dissolution rate of a physiologically active substance of said granular agent is not higher than 50% when measured under the conditions consisting of pH 7.1, 39° C. and 18 hours, and the dissolution rate of said substance of said granular agent is not lower than 20% when measured under the conditions consisting of pH 2, 39° C. and 18 hours; wherein said coating layer has a laminar structure in which said tabular crystals are arranged in a laminated state, said first coating material and said second coating material are in a proportion of 3:2 to 1:3 by weight and said coating layer is present in a coating ratio of 5% by weight or more and 50% by weight or less, based on the total weight of the granular agent.

19. The granular agent used for growing or increasing lactation of ruminants as claimed in claim 18, wherein said physiologically active substance is at least one substance selected from the group consisting of an amino acid, a derivative of an amino acid selected from the group consisting of an N-acylamino acid, a hydroxy homologue compound, a hydrochloride salt of an amino acid, an ammonium salt of an amino acid and a sodium salt of an amino acid, a vitamin, a derivative of a vitamin selected from the group consisting of vitamin A palmitate, vitamin A acetate, menadione sodium bisulfite, thiamine hydrochloride, pyridoxine hydrochloride and p-aminobenzoic acid, an enzyme, an animal drug, a hormone, a carbohydrate, a nutrient protein, a microorganism and a mineral.

20. A granular agent used for growing or increasing lactation of ruminants as claimed in claim 19, wherein said amino acid is at least one substance selected from the group consisting of alanine, glycine, lysine, methionine, tryptophan, arginine, threonine, valine, leucine, isoleucine, histidine, phenylalanine, glutamine, and glutamic acid, wherein said vitamin is at least one substance selected from the group consisting of vitamin A, β-carotene, thiamin, riboflavin, pyridoxine, cyanocobalamin, vitamin D, vitamin E, vitamin K, choline, choline chloride or other choline salt, vitamin C, magnesium salt of L-ascorbyl-2-phosphate, betain, nicotinic acid, nicotinic amide, folic acid, biotin, and pantothenate.

21. A granular agent used for growing or increasing lactation of ruminants as claimed in claim 19, wherein said physiologically active substance is at least one substance selected from the group consisting of alanine, glycine, lysine or lysine hydrochloride, methionine, tryptophan, choline chloride or other choline salt, vitamin C, magnesium salt of L-ascorbyl-2-phosphate, betaine, nicotinic acid, and glucose.

22. A granular agent used for growing or increasing lactation of ruminants comprising a core granular agent containing a physiologically active substance coated with a coating layer comprising:

(a) a first coating material composed of one or more substances selected from the group consisting of a fatty acid having 12 to 22 carbon atoms or ester thereof, an animal or vegetable fat and fatty oil or a hardened animal or vegetable fat and fatty oil, having a melting point of 40° C. or higher, and a wax having a melting point of 40° C. or higher, and (b) a second coating material composed of tabular crystals of a substance which is sparingly water-soluble under a neutral condition but is readily water-soluble under an acidic condition and which has an average particle size of 5 to 30 μm, wherein said physiologically active substance is at least one substance selected from the group consisting of an amino acid, a derivative of an amino acid selected from the group consisting of an N-acylamino acid, a hydroxy homologue compound, a hydrochloride salt of an amino acid, an ammonium salt of an amino acid and a sodium salt of an amino acid, a vitamin, a derivative of a vitamin selected from the group consisting of vitamin A palmitate, vitamin A acetate, menadione sodium bisulfite, thiamine hydrochloride, pyridoxine hydrochloride and p-aminobenzoic acid, an enzyme, an animal drug, a hormone, a carbohydrate, a nutrient protein, a microorganism and a mineral; wherein said coating layer has a laminar structure in which said tabular crystals are arranged in a laminated state, said first coating material and said second coating material are in a proportion of 3:2 to 1:3 by weight and said coating layer is present in a coating ratio of 5% by weight or more and 50% by weight or less, based on the total weight of the granular agent.

23. A granular agent used for growing or increasing lactation of ruminants as claimed in claim 22, wherein said amino acid is at least one substance selected from the group consisting of alanine, glycine, lysine, methionine, tryptophan, arginine, threonine, valine, leucine, isoleucine, histidine, phenylalanine, glutamine, and glutamic acid, wherein said vitamin is at least one substance selected from the group consisting of vitamin A, β-carotene, thiamin, riboflavin, pyridoxine, cyanocobalamin, vitamin D, vitamin E, vitamin K, choline, choline chloride or other choline salt, vitamin C, magnesium salt of L-acorbyl-2-phosphate, betain, nicotinic acid, nicotinic amide, folic acid, biotin, and pantothenate.

24. A granular agent used for growing or increasing lactation of ruminants as claimed in claim 22, wherein said physiologically active substance is at least one substance selected from the group consisting of alanine, glycine, lysine or lysine hydrochloride, methionine, tryptophan, choline chloride or other choline salt, vitamin C, magnesium salt of L-acorbyl-2-phosphate, betaine, nicotinic acid, and glucose.

* * * * *

UNITED STATES PATENT AND TRADEMARK OFFICE
CERTIFICATE OF CORRECTION

PATENT NO. : 5,571,527
DATED : November 5, 1996
INVENTOR(S) : Nishimura et al

It is certified that error appears in the above-indentified patent and that said Letters Patent is hereby corrected as shown below:

Col. 15, line 19, delete "ad" and insert --and--.
Col. 19, delete "acorbyl" and insert --ascorbyl--.
Col. 20, line 26, delete "acorbyl" and insert --ascorbyl--.

Col. 20, line 34, delete "acorbyl" and insert --ascorbyl--.

Signed and Sealed this

Twenty-ninth Day of April, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,571,527
DATED : November 5, 1996
INVENTOR(S) : Nishimura et al

It is certified that error appears in the above-indentified patent and that said Letters Patent is hereby corrected as shown below:

Col. 15, line 19, delete "ad" and insert --and--.

Col. 20, line 26, delete "acorbyl" and insert --ascorbyl--.

Col. 20, line 34, delete "acorbyl" and insert --ascorbyl--.

This certificate supersedes Certificate of Correction issued April Twenty-ninth, 1997.

Signed and Sealed this

Second Day of September, 1997

BRUCE LEHMAN

*Attest:*

*Attesting Officer*  *Commissioner of Patents and Trademarks*